United States Patent [19]

Baltes et al.

[11] Patent Number: 4,568,777

[45] Date of Patent: Feb. 4, 1986

[54] PROCESS FOR ISOMERIZING MONOCHLOROPHENOLS OR DICHLOROPHENOLS

[75] Inventors: Herbert Baltes, Frankfurt am Main; Ernst I. Leupold, Neu-Anspach, both of Fed. Rep. of Germany

[73] Assignee: Hoechst Aktiengesellschaft, Frankfurt, Fed. Rep. of Germany

[21] Appl. No.: 670,148

[22] Filed: Nov. 9, 1984

[30] Foreign Application Priority Data

Nov. 12, 1983 [DE] Fed. Rep. of Germany ....... 3340997
Dec. 17, 1983 [DE] Fed. Rep. of Germany ....... 3345808

[51] Int. Cl.$^4$ .............................................. C07C 39/27
[52] U.S. Cl. .................................................. 568/774
[58] Field of Search ....................................... 568/774

[56] References Cited

U.S. PATENT DOCUMENTS 3,293,309  12/1966  Zemba ................................. 568/774
3,681,467  8/1972   O'Bara ................................. 568/774
4,447,660  5/1984   Jouannetaud et al. ............. 568/774

Primary Examiner—Werren B. Lone
Attorney, Agent, or Firm—Curtis, Morris & Safford

[57] ABSTRACT

The invention relates to a process for isomerizing monochlorophenols or dichlorophenols in which one or more monochlorophenol or dichlorophenol is passed in the gas phase over a zeolite catalyst. In particular, the invention relates to a process for preparing 3-chlorophenol by isomerizing 2-chlorophenol and/or 4-chlorophenol and to a process for preparing 2,5-dichlorophenol by isomerizing 2,4-dichlorophenol using said method.

12 Claims, No Drawings

PROCESS FOR ISOMERIZING MONOCHLOROPHENOLS OR DICHLOROPHENOLS

The invention relates to a process for isomerizing monochlorophenols and dichlorophenols.

Monochlorophenols are industrially commonly prepared by chlorinating phenol. The reaction produces mixtures of the two isomers 2- and 4-chlorophenol in a ratio which can be varied within wide limits through the choice of suitable reaction conditions (Houben-Weyl, Methoden der Organischen Chemie (Methods of Organic Chemistry), Volume V/3, Halogen Compounds, Stuttgart 1962, page 679).

3-Chlorophenol cannot be prepared in this way, but is prepared by diazotizing 3-chloroaniline and boiling the diazonium salt (Ullmanns Enzyklopädie der Technischen Chemie (Ullmann's Encyclopedia of Industrial Chemistry), 4th Edition, Volume 9, page 574). This multistage synthesis is technically complicated and costly.

Simple and economical methods of preparing 3-chlorophenol on an industrial scale have hitherto not been described.

Dichlorophenols are likewise industrially commonly prepared by ring-chlorinating phenol. The reaction initially produces a mixture of o- and p-chlorophenol which on further chlorination leads to 2,4-dichlorophenol and—to a lesser extent—2,6-dichlorophenol (Houben-Weyl, Methoden der Organischen Chemie (Methods of Organic Chemistry), Volume V/3, Halogen Compounds, Stuttgart 1962, page 680).

The other four isomers of dichlorophenol cannot be prepared by direct chlorination. Their preparation requires in some cases technically complicated and costly multistage syntheses. 2,3-Dichlorophenol, for example, can be prepared by sulfonating 1,2,3-trichlorobenzene and then hydrolyzing. 3,4-Dichlorophenol can be synthesized oxidatively from 3,4-dichlorocumine; other methods include the Sandmeyer diazotization, partial hydrolysis of trichlorobenzenes, and partial hydrogenation of polychlorinated phenols (Kirk-Othmer, Encyclopedia of Chemical Technology, 3rd Edition, Volume 5, page 866).

Simple and economical methods of preparing 2,3-dichlorophenol, 2,5-dichlorophenol, 3,4-dichlorophenol and 3,5-dichlorophenol on an industrial scale have hitherto not been described.

The present invention provides a process for isomerizing monochlorophenols or dichlorophenols, which comprises passing at least one monochlorophenol or dichlorophenol in the gas phase over a zeolite catalyst. More particularly, the present invention provides a process for preparing 3-chlorophenol, which comprises passing 2-chlorophenol and/or 4-chlorophenol in the gas phase over a zeolite catalyst. The present invention also provides a process for preparing 2,5-dichlorophenol by isomerizing 2,4-dichlorophenol in the gas phase over a zeolite catalyst.

On the basis of the state of the art it was surprising and completely unforeseeable that monochlorophenols can be isomerized so simply, and in particular that 3-chlorophenol, previously so difficult to prepare, can be prepared so easily from industrially readily accessible 2-chlorophenol, 4-chlorophenol or mixtures thereof.

To isomerize the monochlorophenols, one of the monochlorophenols or a mixture of two monochlorophenols or a mixture of all three monochlorophenols is passed either alone or together with one or more organic diluents in gas form over the zeolite catalyst. It is particularly important to use the isomeric mixture which is formed on chlorinating phenol.

It was just as surprising that dichlorophenols can be isomerized so simply and that dichlorophenols which were previously difficult to prepare can be prepared so easily from technically readily accessible dichlorophenols, like 2,5-dichlorophenol from 2,4-dichlorophenol.

To isomerize the dichlorophenols, one of the dichlorophenols or a mixture of dichlorophenols is passed either alone or together with one or more organic diluents in gas form over the zeolite catalyst. The most important starting material is 2,4-dichlorophenol, which is available on an industrial scale, or a mixture of dichlorophenols as formed on chlorinating phenol.

Suitable organic diluents are in particular aromatic hydrocarbons, preferably chlorobenzene, benzene and/or toluene. The molar ratio of diluent to dichlorophenol is generally 0:1 to 10:1, preferably 0:1 to 3:1.

Suitable zeolites are generally both natural and synthetic zeolites, preferably synthetic zeolites of the pentasil, mordenite or faujasite type, in particular synthetic zeolites of the pentasil type.

For the purposes of the present invention, pentasils are as defined by Kokotailo and Meier ("Pentasil family of high silicon crystalline materials" in Special Publication No. 33 of the Chemical Society, London, 1980). The pentasil family includes for example the synthetic zeolites ZSM-5 (U.S. Pat. No. 3,702,886), ZSM-8 (British Pat. No. 1,334,243), ZSM-11 (U.S. Pat. No. 3,709,979) and ZSM-23 (U.S. Pat. No. 4,076,842).

The silicon/aluminum ratio of the pentasils is preferably within the range from 20 to 2,000, and that of the mordenites preferably within the range from 5 to 100. Pentasils or mordenites having a higher aluminum content can be brought to the desired silicon/aluminum ratio by treatment with mineral acids, organic acids or kelating substances to remove part of the aluminum out of the zeolite lattice.

In the process according to the invention, the zeolites are generally used in their acid form. These acid forms can be prepared by methods known per se, viz. complete or partial ion exchange, from the alkali metal forms in which they are as a rule obtained in zeolite synthesis or in which they occur as natural products. The preferred acid forms are partially or completely exchanged H- or ammonium forms, in particular H-forms. A conventional way of preparing the H-form of a zeolite comprises, for example, first of all converting the alkali metal form by partial or complete ion exchange with an ammonium salt solution into the ammonium form and then converting the ammonium form by calcining into the H-form. However, even the forms which have been partially or completely exchanged with alkali metal, alkaline earth metal or rare earth metal ions are catalytically active.

The zeolite catalysts according to the invention generally consist of the catalytically active zeolite component plus a binder material. The latter is required to bring the zeolite into an external form suitable for the process according to the invention.

Suitable binder materials are in particular oxides or hydroxides of aluminum, of silicon and of titanium, and layer silicates, for example from the kaolin or montmorillonite family.

This zeolite catalyst thus prepared is usually activated before use in the isomerization reaction according to the invention by calcining at temperatures between 300° and 700° C. To improve the stability of the catalyst it is sometimes advantageous to carry out the calcination in the presence of steam, ammonia or mixtures thereof.

It has been found to be advantageous to admix hydrogen to the gaseous starting material (at least one monochlorophenol or dichlorophenol) or to the gaseous mixture of starting material and organic diluent. Furthermore, it can also be advantageous to admix a carrier gas which is inert under the reaction conditions. Examples of suitable carrier gases are nitrogen and noble gases. Hydrogen and/or the carrier gas are added in such an amount that the residence time is between 1 and 10 s.

The isomerization according to the invention is generally carried out at temperatures between 300° and 550° C., preferably at 320° to 450° C., under pressures of 0.1 to 100 bar, preferably under 1-40 bar, in particular under atmospheric pressure.

The load on the zeolite catalyst, expressed as LHSV (Liquid Hourly Space Velocity, $h^{-1}$), is generally between 0.1 and 10 $h^{-1}$, preferably between 0.3 and 5 $h^{-1}$.

An advantageous, simple way of carrying out the novel isomerization of monochlorophenols comprises passing the starting material or the mixture of starting material and organic diluent from a metering apparatus into a vaporization zone, and then passing the resulting gas through an externally heated reaction tube which contains the catalyst.

An advantageous, simple way of carrying out the novel isomerization of dichlorophenols comprises passing the starting material in the form of a melt or in the form of a solution in an organic diluent from a metering apparatus into a vaporization zone, and then passing the resulting gas through an externally heated reaction tube which contains the catalyst.

It is in the vaporization zone where the hydrogen and/or the inert carrier gas, if used, are admixed; it has been found to be advantageous to heat these gases up to the reaction temperature before they are mixed in. After leaving the reactor the reaction products are cooled down to separate off the condensible portions. The isomerization according to the invention, however, is not restricted to this (fixed-bed reactor) procedure, but can in principle also be carried out in other reactors which are suitable for gas phase reactions, for example in a fluidized-bed reactor. It is also possible to carry out the reaction in the liquid phase.

The resulting isomeric mixtures can be separated into their components using known methods, such as distillation, fractional crystallization, extraction or a combination of these methods.

The following examples illustrate the invention without limiting it in any way.

EXAMPLE 1

A. Preparation of the catalyst

Pulverulent ZSM-5 zeolite having a silicon-/aluminum ratio of 24:1 was extruded in the presence of 40% by weight of $Al_2O_3$ as binder in the form of pellets, which were dried at 120° C. for 12 hours and were calcined at 500° C. in an air stream in the course of 4' hours. Afterwards the pellets were exchanged at 90° C. 5 times with 10% strength by weight ammonium chloride solution, were washed thoroughly with water, were dried at 120° C. for 12 hours and were calcined once more at 500° C. in air in the course of 4 hours. The pellets were then comminuted. The fraction of particles which were 1.0 to 1.5 mm in diameter was classified out for the isomerization experiment. The catalyst was activated at 450° C. for a further 2 hours before each isomerization experiment.

B. Implementation of the isomerization 9 ml of 2-chlorophenol per hour were plungered into an upright glass reactor of 150 mm in length and 20 mm in diameter by way of a vaporization zone. At the same time said vaporization zone was supplied at a rate of 3 liters per hour with hydrogen which had been heated up to 400° C. beforehand.

The reactor was likewise heated to 400° C. from the outside and contained 15 ml of the zeolite catalyst (H-ZSM-5) described above. The temperature in the interior of the reactor was measured with a thermocouple. The reaction products were condensed into a −70° C. cold trap.

After a startup time of 1 hour to allow for constant operating conditions to become established, the actual catalyst test was carried out for a period of 2 hours. The condensate was analyzed by gas chromatography.

The composition of the product mixture and the selectivities can be seen in Table 1.

EXAMPLE 2

12 ml per hour of a solution of 50% by weight of 4-chlorophenol and 50% by weight of chlorobenzene were passed analogously to Example 1 into the apparatus described there, together with 5 liters of oxygen per hour. The reactor contained 15 ml of H-ZSM-5 as in Example 1 and was heated up to 380° C. The result of a 2-hour experiment can be seen in Table 1.

EXAMPLE 3

15 ml of 2-chlorophenol and 10 liters of hydrogen were passed per hour at 400° C. over 15 ml of H-mordenite analogously to Example 1. Table 1 shows the result of a 2-hour experiment.

TABLE 1

| Starting isomer: | Example 1 2-chloro-phenol | Example 2* 4-chloro-phenol | Example 3 2-chloro-phenol |
|---|---|---|---|
| Composition of the end product (% by weight) | | | |
| 2-chlorophenol | 48.2 | 3.1 | 67.4 |
| 3-chlorophenol | 34.4 | 17.3 | 23.4 |
| 4-chlorophenol | 7.4 | 28.4 | 3.4 |
| phenol | 6.4 | 2.1 | 1.1 |
| Selectivity for 3-chlorophenol (%) | 65.3 | 68.3 | 70.6 |

*the product mixture also contains 47.2% by weight of chlorobenzene (diluent).

EXAMPLE 4

A. Preparation of the catalyst

As in Example 1

B. Implementation of the isomerization 9 ml per hour of a solution of 50% by weight of 2,4-dichlorophenol and 50% by weight of chlorobenzene were plungered into an upright glass reactor of 150 mm in length and 20 mm in diameter by way of a vaporization zone. At the same time said vaporization zone was supplied at a rate of 3 liters per hour with hydrogen which had been heated up to 400° C. beforehand.

The reactor was likewise heated to 400° C. from the outside and contained 15 ml of the zeolite catalyst (H-ZSM-5) described above. The temperature in the interior of the reactor was measured with a thermocouple. The reaction products were condensed into a −70° C. cold trap.

After a startup time of 1 hour to allow for constant operating conditions to become established, the actual catalyst test was carried out for a period of 2 hours. The condensate was analyzed by liquid chromatography.

The result can be seen in Table 2.

EXAMPLE 5

About 6 ml/h of 2,4-dichlorophenol were passed in the form of a melt from a hot dropping funnel at 70° C. into an evaporator, where they vaporized at 350° C. In the evaporator, the 2,4-dichlorophenol vapor was mixed with nitrogen (10 liters/hour). This mixture was then passed into the H-ZSM-5-containing reactor described in Example 4. The reactor was heated to 380° C. The result of a 2-hour experiment can be seen in Table 2.

EXAMPLE 6

12 ml/h of a 50% by weight strength solution of 2,5-dichlorophenol in chlorobenzene were passed analogously to Example 4 into the apparatus described there, together with 5 liters of nitrogen per hour. The reactor contained 15 ml of H-ZSM-5 as in Example 4 and was heated up to 400° C. The result of a 2-hour experiment can be seen in Table 2.

EXAMPLE 7

9 ml/h of a 40% by weight strength solution of 2,3-dichlorophenol in chlorobenzene were passed analogously to Example 4 into the apparatus described there, together with 5 liters of nitrogen per hour. The reactor contained 15 ml of H-ZSM-5 ano was heated up to 430° C. The result of a 2-hour experiment can be seen in Table 2.

TABLE 2

| starting isomer: | Example 4 2,4-dichlorophenol | Example 5 2,4-dichlorophenol | Example 6 2,5-dichlorophenol | Example 7 2,3-dichlorophenol |
|---|---|---|---|---|
| Yield (% by weight weight) of | | | | |
| 2,3-dichlorophenol | 0.6 | 0.5 | 3.5 | A[1] |
| 2,4-dichlorophenol | A[1] | A[1] | 15.4 | 4.0 |
| 2,5-dichlorophenol | 26.4 | 8.3 | A[1] | 8.0 |
| 2,6-dichlorophenol | <0.1 | <0.1 | <0.1 | <0.1 |
| 3,4-dichlorophenol | <0.1 | <0.1 | 2.8 | <0.1 |
| 3,5-dichlorophenol | <0.1 | <0.1 | <0.1 | <0.1 |
| chlorophenols | 4.2 | 1.2 | 5.2 | 2.2 |
| Selectivity (%) for dichlorophenols | 67.4 | 64.2 | 68.1 | 66.3 |

A[1] = starting isomer

We claim:

1. A process for preparing 3-chlorophenol, which comprises contacting 2-chlorophenol and/or 4-chlorophenol in the gas phase with a zeolite catalyst of the pentasil, mordenite or faujasite type at a temperature between 300° and 550° C.

2. The process as claimed in claim 1, wherein the zeolite is of the pentasil type.

3. The process as claimed in claim 1, wherein the zeolite is in its acid form.

4. The process as claimed in claim 2, wherein the zeolite is in its acid form.

5. The process as claimed in claim 1, wherein the zeolite contains protons as cations.

6. The process as claimed in claim 2, wherein the zeolite contains protons as cations.

7. A process for preparing 2,5-dichlorophenol, which comprises contacting 2,4-dichlorophenol in the gas phase with a zeolite catalyst of the pentasil, mordenite or faujasite type at a temperature between 300° and 550° C.

8. The process as claimed in claim 7, wherein the zeolite is of the pentasil type.

9. The process as claimed in claim 7, wherein the zeolite is in its acid form.

10. The process as claimed in claim 8, wherein the zeolite is in its acid form.

11. The process as claimed in claim 7, wherein the zeolite contains protons as cations.

12. The process as claimed in claim 8, wherein the zeolite contains protons as cations.

* * * * *